(12) United States Patent
Collazo et al.

(10) Patent No.: US 7,344,542 B2
(45) Date of Patent: Mar. 18, 2008

(54) PIN EXTRACTION ASSEMBLY

(75) Inventors: Carlos E. Collazo, Old Greenwich, CT (US); Scott Logan, Ringwood, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 170 days.

(21) Appl. No.: 11/062,009

(22) Filed: Feb. 18, 2005

(65) Prior Publication Data
US 2006/0200159 A1   Sep. 7, 2006

(51) Int. Cl.
*A61B 17/58* (2006.01)
(52) U.S. Cl. .................................................... 606/88
(58) Field of Classification Search ............ 606/62–64, 606/86–89, 96–98
See application file for complete search history.

(56) References Cited

U.S. PATENT DOCUMENTS

| | | | |
|---|---|---|---|
| 4,524,766 A | 6/1985 | Petersen | |
| 5,197,944 A | 3/1993 | Steele | |
| 5,306,276 A * | 4/1994 | Johnson et al. | 606/86 |
| 5,578,039 A * | 11/1996 | Vendrely et al. | 606/88 |
| 5,628,750 A * | 5/1997 | Whitlock et al. | 606/88 |
| 5,643,272 A * | 7/1997 | Haines et al. | 606/80 |
| 5,704,941 A * | 1/1998 | Jacober et al. | 606/88 |
| 5,916,219 A * | 6/1999 | Matsuno et al. | 606/88 |
| 6,090,114 A | 7/2000 | Matsuno et al. | |
| 6,267,762 B1 * | 7/2001 | Millard et al. | 606/54 |
| 6,595,997 B2 * | 7/2003 | Axelson et al. | 606/88 |
| 2004/0122436 A1 * | 6/2004 | Grimm | 606/87 |
| 2004/0153084 A1 * | 8/2004 | Haney et al. | 606/87 |

OTHER PUBLICATIONS

U.S. Appl. No. 10/782,615, filed Feb. 18, 2004, Collazo.

* cited by examiner

*Primary Examiner*—Eduardo C. Robert
*Assistant Examiner*—Michael J Araj
(74) *Attorney, Agent, or Firm*—Lerner, David, Littenberg, Krumholz & Mentlik, LLP

(57) ABSTRACT

A tibial alignment guide assembly for positioning a resection guide, the assembly including a main shaft having a proximal end and a distal end. The assembly also includes an anchor arm having an engaging end and a connection end. The connection end is preferably attached to the proximal end of the main shaft and the engaging end preferably has at least one anchor pin extending outwardly therefrom. The at least one anchor pin is adapted to anchor the tibial alignment guide assembly to a tibia plateau in order that the resection guide may be correctly aligned to the tibia. The assembly further includes a lever including an actuation end and a handle. The lever is pivotally connected to the anchor arm, whereby movement of the lever while the actuation end bears against the tibia plateau surface, causes at least a partial extraction of the at least one anchor pin from the tibia plateau.

17 Claims, 7 Drawing Sheets

PIN EXTRACTION ASSEMBLY

BACKGROUND OF THE INVENTION

The present invention is directed to a tibial alignment guide assembly and a method of using a tibial alignment guide assembly during arthroplastic surgery of the knee, particularly for the extraction of tibial plateau fixation pins that hold the assembly in place as the tibial alignment guide is being positioned and fixed for tibial resection.

In replacing a knee joint, it is important that the bone at the proximal end of the tibia be removed or resected with respect to the mechanical axis of the tibia and taking into account the appropriate varus/valgus angle and flexion/extension angle for the knee joint. As resected, and with the femur resected, the resected end of the tibia can then receive a tibial implant and the resected end of the femur can receive a femoral implant to reconstruct the knee joint. Proper fit and function of the implant will depend on the accuracy of the resections. Therefore, a resection guide may be affixed to the tibia to direct a cutting instrument along the correct plane.

One method used for obtaining the correct bone cuts includes providing a tibial alignment guide assembly that is anchored relative to the tibia for alignment of the tibial resection. The tibial alignment guide assembly generally includes an ankle clamp mounted thereon for stabilizing a distal end of the tibial alignment guide assembly to the lower leg, i.e., ankle, and a means for anchoring an end of the tibial alignment guide assembly directly to the tibia. The latter usually includes at least one pin or spike extending outwardly from the tibial alignment guide assembly. With the ankle clamp secured to the ankle, the resection guide is brought proximate with the tibia. At this point, the at least one pin or spike is driven by impaction into the tibia thereby anchoring the tibial alignment guide assembly relative to the tibia. The resection guide may now be correctly aligned with the tibia, using the tibial alignment guide assembly as a reference.

The resection guide itself is next affixed to the tibia in a desired position, again using the tibial alignment guide assembly as a reference. Once the resection guide is affixed to the tibia, the rest of the tibial alignment guide assembly is removed so that the surgeon can make the various cuts to the proximal end of the tibia.

In order to remove the rest of the tibial alignment guide assembly, the ankle clamp is separated from the ankle and the fixation pin is extracted from the proximal end of the tibia. Extracting the fixation pin may include striking a part of the tibial alignment guide assembly with a hammer in order to dislodge the pin from the tibia or attaching and using a slap hammer to dislodge the pins.

Unfortunately, this method of extracting the fixation pin includes additional steps and instruments. The time and expense of the surgery is thus extended, and there is additional time involved in maintaining the additional instruments. Perhaps most importantly, an extraction hammer exerts an uncontrolled sudden force against the tibial alignment guide assembly, the excessive jarring may cause movement of the resection guide, thereby displacing it from its desired spatial relationship with the tibia. Even slight movement of the resection guide relative to the tibia may lead to resection in the wrong plane, or if noticed by the surgeon, the need for realignment of the resection guide.

Such a resection guide is shown in U.S. Pat. No. 6,090,114, the disclosure of which is hereby incorporated by reference herein.

SUMMARY OF THE INVENTION

The present invention can be adapted for most situations where anchor pins or fixation devices anchor an assembly to a bone and where a controlled force for removing the fixation device from the bone is desired.

In one preferred embodiment of the present invention, a tibia alignment guide assembly may be provided including a main shaft having a proximal end and a distal end. The main shaft is adapted for juxtaposition with the tibia in order to assist in the positioning of a resection guide. The tibial alignment guide assembly may also include an anchor arm having an engaging end and a connection end with preferably the connection end being attached to the proximal end of the main shaft. The engaging end preferably includes at least one anchor pin extending outwardly therefrom. The at least one anchor pin is adapted to anchor the tibial alignment guide assembly to a tibia plateau in order that the resection guide may be correctly aligned to the tibia. The tibial alignment guide assembly also preferably includes a lever having an actuation end and a handle. The lever is preferably pivotally connected to the anchor arm, whereby movement of the lever while the actuation end bears against the tibial plateau surface causes at least the partial extraction of the at least one anchor pin from the tibial plateau.

The tibial alignment guide assembly may also include a pivot pin which is placed into a first aperture of the anchor arm and second and third apertures of the lever so as to pivotally connect the two. In an alternate embodiment, the lever may only include a single aperture which receives the pivot pin.

In yet another embodiment, the anchor arm may include an exterior surface having a pivot pin extending radially outward from the exterior surface. The pivot pin of the anchor arm may be received within an aperture of the lever so as to pivotally connect the two together. The tibial alignment guide assembly may also include a resection guide connectable to the main shaft. The anchor pins of the present invention may be either integrally formed with the anchor arm or be separate and discrete elements.

In yet another aspect, the present invention may be adapted to work with various bone alignment guides and may include an anchor arm having an engagement means for engaging a bone in order that the bone alignment guide assembly is affixed to the bone. Additionally, the bone alignment guide assembly may also include a lever including extraction means for initiating extraction of the engagement means of the anchor arm from the bone.

In one method of the present invention, a patient's proximal tibia may be prepared for surgery, the method including the steps of positioning a resection guide in a desired spatial relationship relative to the tibia and anchoring a tibial alignment guide assembly to a proximal tibial. The resection guide may next be secured to the tibia and then removal of at least a portion of the tibial alignment guide assembly from the proximal tibia may be initiated by actuating a lever. The step of anchoring the tibial alignment guide assembly may include urging at least one anchor pin into engagement with the proximal tibia. In addition, the step of initiating removal of at least a portion of the tibial alignment guide assembly may include initiating removal of the at least one anchor pin from engagement with the proximal tibia. The actuating of the lever may include bringing the lever into contact with the proximal tibia.

In an alternate method of the present invention, a knee joint may be restructured including the steps of positioning a resection guide in a desired spatial relationship relative to the tibia and anchoring a tibial alignment guide assembly to a proximal tibia. Next, the resection guide is secured to the tibia. Subsequently, at least removal or at least a portion of the tibia alignment guide assembly from the proximate tibia is initiated by actuating a lever connected to the tibial alignment guide assembly.

The proximal tibia may then be further prepared to receive a tibia implant and additionally the femur may also be prepared for a femoral implant. Once the femur and tibial are prepared, the tibial implant and the femoral implant may be implanted so as to reconstruct a knee joint.

In a further aspect of the present invention, a patella may be prepared to receive a patella implant with the patella implant also being implanted.

DETAILED DESCRIPTION

The present invention is directed to an extramedullary tibial alignment guide assembly having a proximal pin extraction lever, although the present invention may be adapted for use of extracting various pins from various bones. The tibial alignment guide assembly is designed to be affixed to a tibia bone and provide an extramedullary reference for positioning a resection guide relative to the tibia bone. The resection guide is affixed to the tibia to direct a cutting instrument along the correct plane for preparing the tibia to receive a tibial implant.

Figure 1:
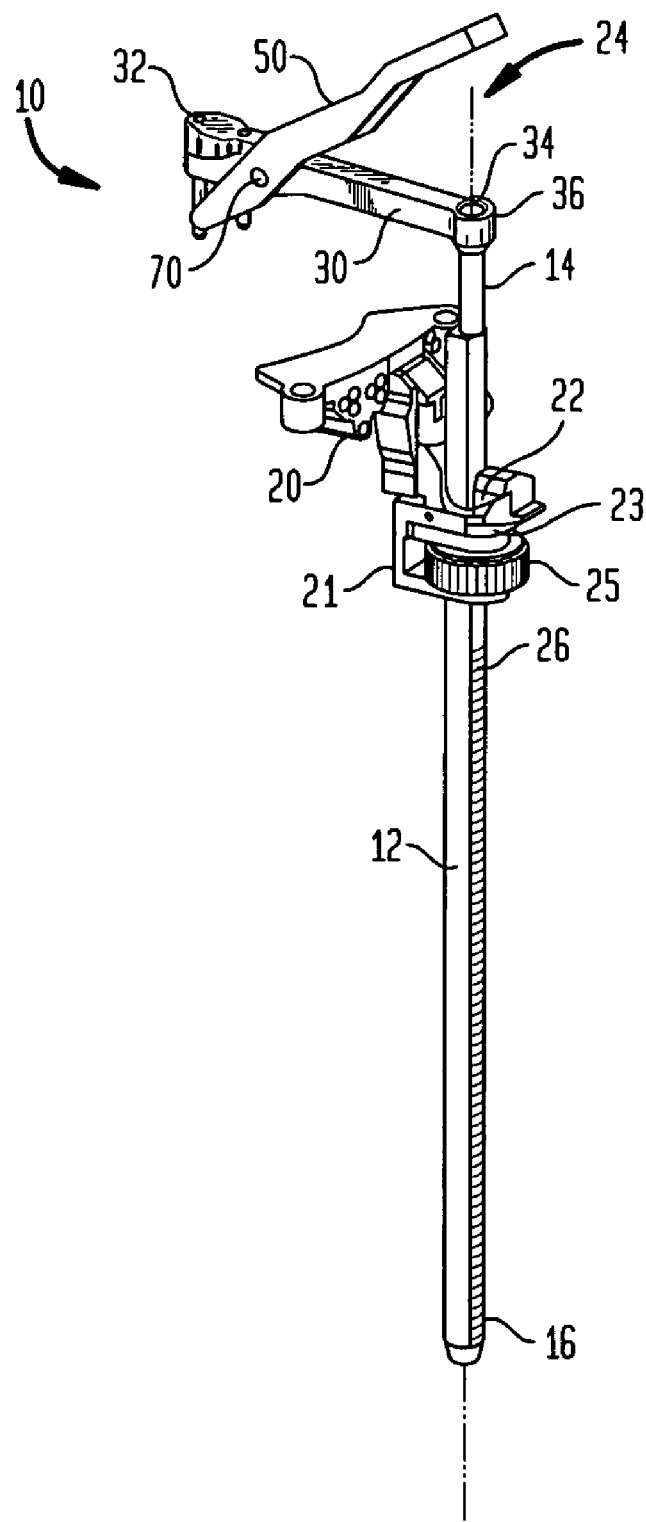
FIG. 1 is a perspective view of one embodiment of the tibial alignment guide assembly of the present invention.

As shown in FIG. 1, a tibial alignment guide assembly 10 preferably includes a main shaft 12 having a proximal end 14 and a distal end 16. Tibial alignment guide assembly 10 also includes a resection guide 20, that is attached to and moveable about main shaft 12. Resection guide 20 is attached to main shaft 12 in a removable manner and may be attached to main shaft 12 by various techniques know in the art.

For instance, as shown in FIG. 1, resection guide 20 may include a mounting block 21 having an aperture 22 defined by a circular wall 23. Aperture 22 is designed to receive distal end 16 of main shaft 12, therein. With distal end 16 disposed within aperture 22, resection guide 20 may be translated along a longitudinal axis 24 of main shaft 12 to anyone of a number of positions along the main shaft. Various features known in the art may be provided in order to aid in the movement of resection guide 20 about main shaft 12, such as but not limited to a thumbscrew 25 attached to the resection guide and threads 26 disposed along an exterior of the main shaft. Thumbscrew 25 includes internal threads (not shown in the figures) that engage threads 26 of main shaft 12. The interaction between the two threads preferably permits the adjustment of resection guide 20 relative to main shaft 12. Thus, resection guide 20 may be moved about main shaft 12 and placed in a desired position. Such a resection guide is shown in U.S. patent application Ser. No. 10/782,615 filed Feb. 19, 2004, the teachings of which are incorporated herein by reference.

Tibial alignment guide assembly 10 also includes anchor arm 30 extending outwardly and transverse to main shaft 12. In one preferred embodiment as shown in FIG. 1, anchor arm 30 is attached to main shaft 12 approximate proximal end 14. Anchor arm 30 preferably includes a first end 32 and a connecting end 34. Connecting end 34 may include a threaded aperture 36 that receives and engages threads (not shown in the figures) disposed on an exterior of proximal end 14 of main shaft 12, thereby allowing anchor arm 30 to be connected to main shaft 12, as shown in FIG. 1. Although FIG. 1 illustrates one embodiment of the present invention, anchor arm 30 may be attached to main shaft 12 using various techniques known in the art such as, but not limited to, riveting the two elements together, welding the two elements or the two elements being integral with one another.

Tibial alignment guide assembly further includes an extraction lever 50 pivotally connected to anchor arm 30, the features and purpose of which will be described below.

Figure 2:
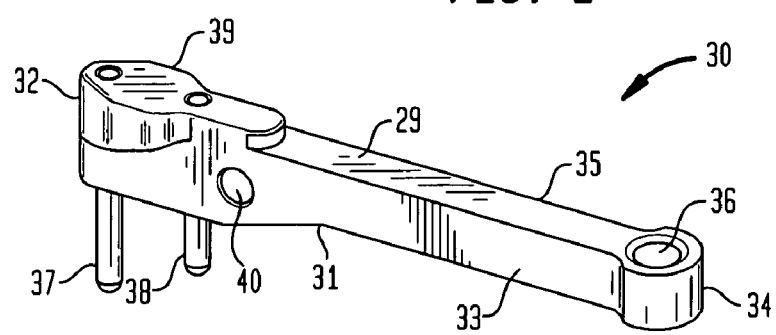
FIG. 2 is a perspective view of an anchor arm used in the assembly of FIG. 1.

With reference to FIG. 2, anchor arm 30 will now be more fully described. As previously mentioned, anchor arm 30 includes first end 32 and connecting end 34. Anchor arm 30 also includes top surface 29, bottom surface 31, and sidewalls 33 and 35. Extending downwardly from bottom surface 31 of anchor arm 30 are anchor pins 37 and 38. Anchor pins 37 and 38 may either extend from bottom surface 31 or be partly disposed within the anchor arm itself. In one preferred embodiment, as shown in the figures, first end 32 preferably includes a shield 39 disposed at top surface 29 of anchor arm 30. Shield 39 is designed to receive a force for example from a hammer, while reducing any damage to the anchor arm itself. Anchor arm 30 preferably also includes an aperture 40 extending from sidewall 33 to sidewall 35.

Figure 3:
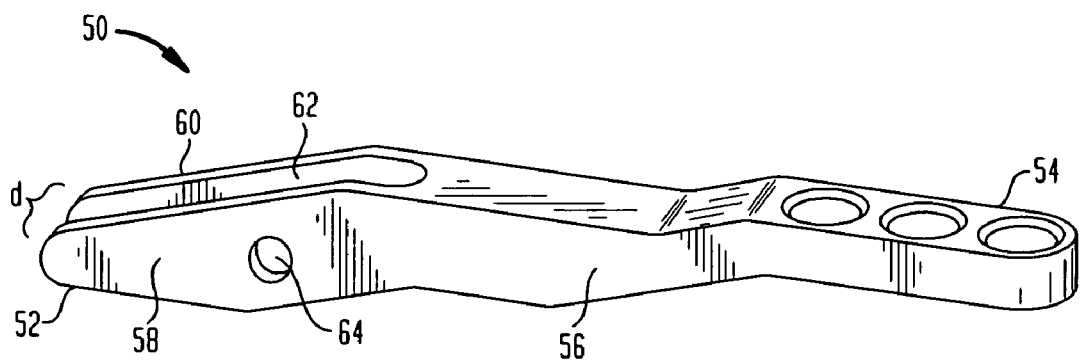
FIG. 3 is a perspective view of an extraction lever used in the present invention.
Figure 4:
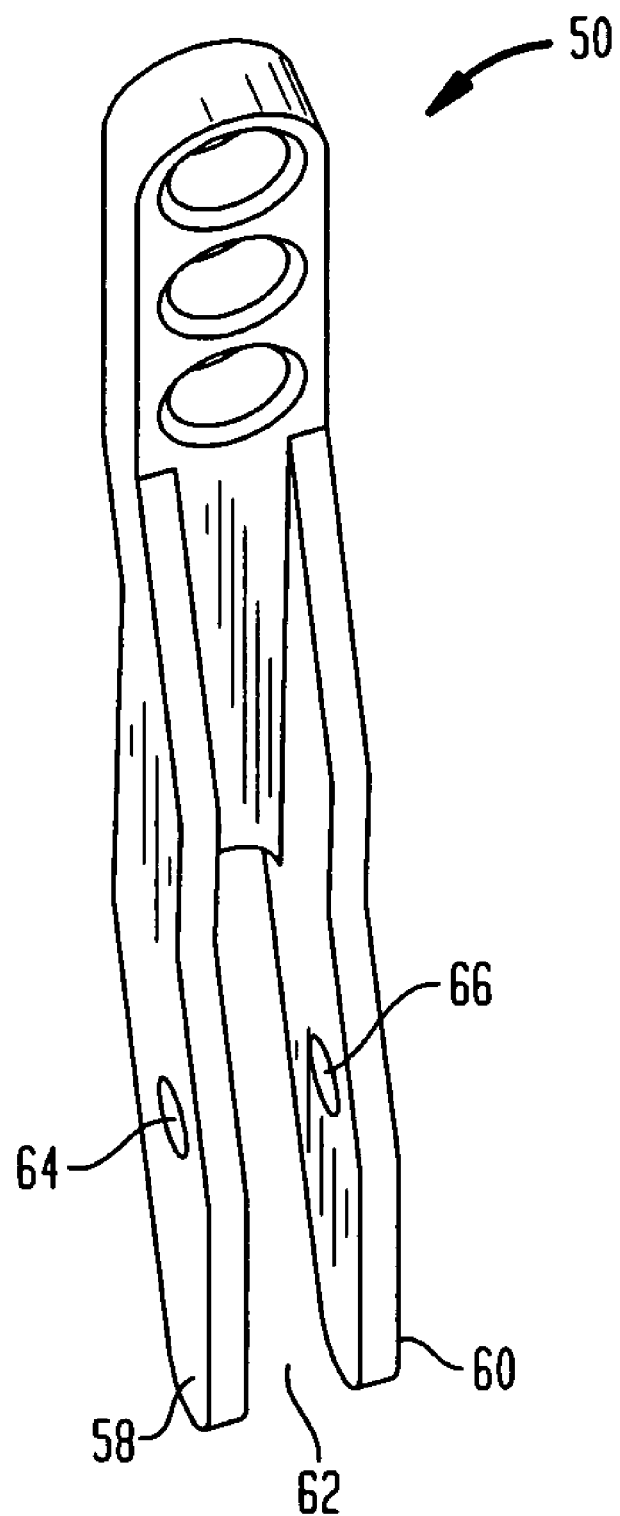
FIG. 4 is a bottom perspective view of the apparatus of FIG. 3.

As shown in FIGS. 3 and 4, extraction lever 50 includes an actuation end 52, a handle 54 remote from the actuation end and a body 56 disposed between the actuation end and the handle. In one preferred embodiment, actuation end 52 is bifurcated or forked and includes a first extension 58 and a second extension 60 extending outwardly from body 56. First extension 58 and second extension 60 are remote from one another and form a gap 62 therebetween. Preferably the extensions are separated by a distance d, as shown in FIG. 3. First extension 58 includes a first aperture 64 extending therethrough and second extension 60 includes a second aperture 66 extending therethrough. In a preferred embodiment, first aperture 64 and second aperture 66 are concentric and have substantially the same diameter.

As shown in FIG. 1, in a method of assembly, extraction lever 50 receives anchor arm 30 within gap 62. Anchor arm 30 preferably has a thickness from sidewall 33 to sidewall 35 slightly less than the distance d between first extension 58 and second extension 60 of extraction lever 50. This design permits anchor arm 30 to be easily disposed within gap 62 and still allow movement between anchor arm 30 and extraction lever 50. In this configuration, first extension 58 is disposed adjacent to sidewall 33 of anchor arm 30 and second extension 60 is disposed adjacent to sidewall 35 of the anchor arm. In a preferred embodiment, first and second extensions 58, 60 are positioned adjacent to sidewalls 33 and 35, respectively, with first aperture 64 and second aperture 66 of their respective extensions, aligned and concentric with aperture 40 of anchor arm 30. With apertures 64, 66 and 40 aligned and concentric, a rod or pivot pin 70 may be slidably received within all three apertures thereby pivotally connecting extraction lever 50 to anchor arm 30. Although, anchor arm 30 and extraction lever 50 are described as being pivotally connected using a rod or pin, various other connectors which allow pivoting may be used including a rivet or the like.

Figure 5:
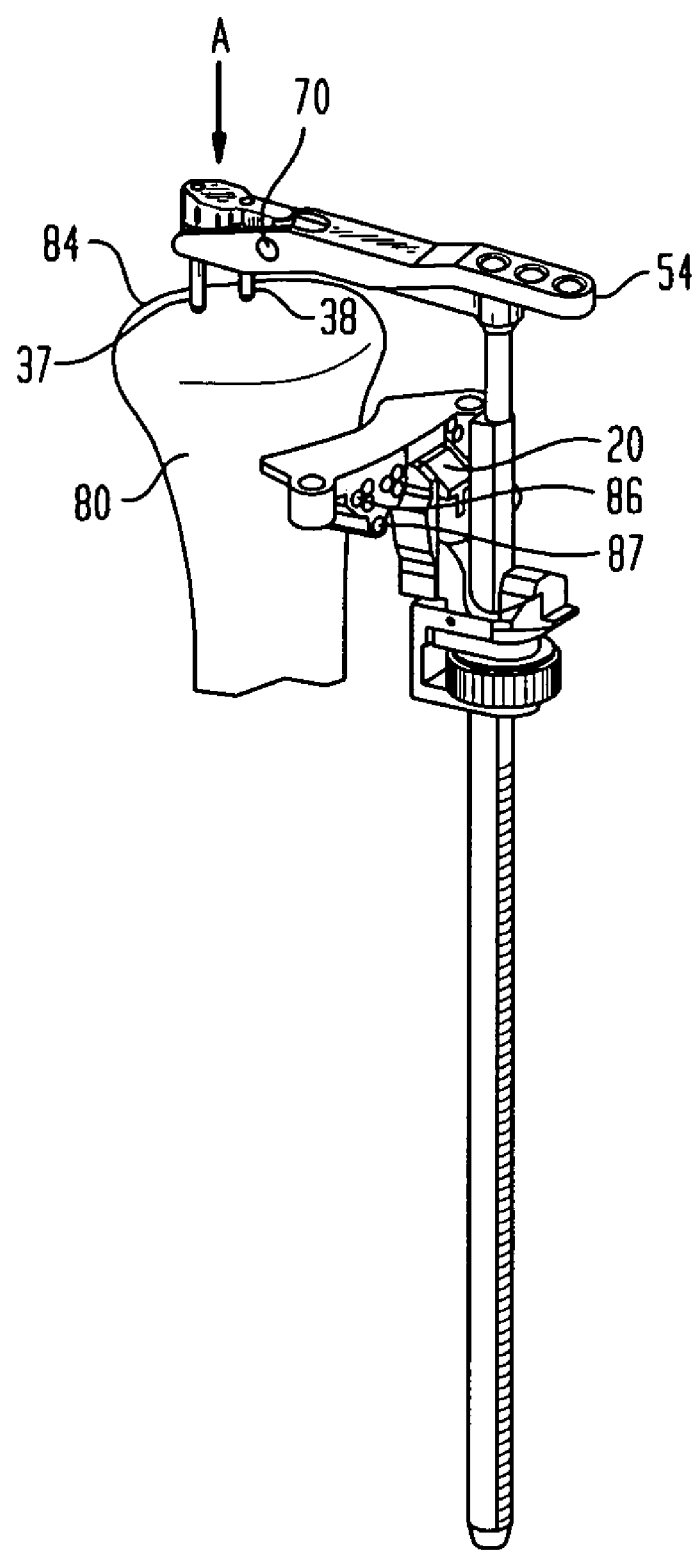
FIG. 5 is a perspective view illustrating the present invention in the released position.
Figure 6:
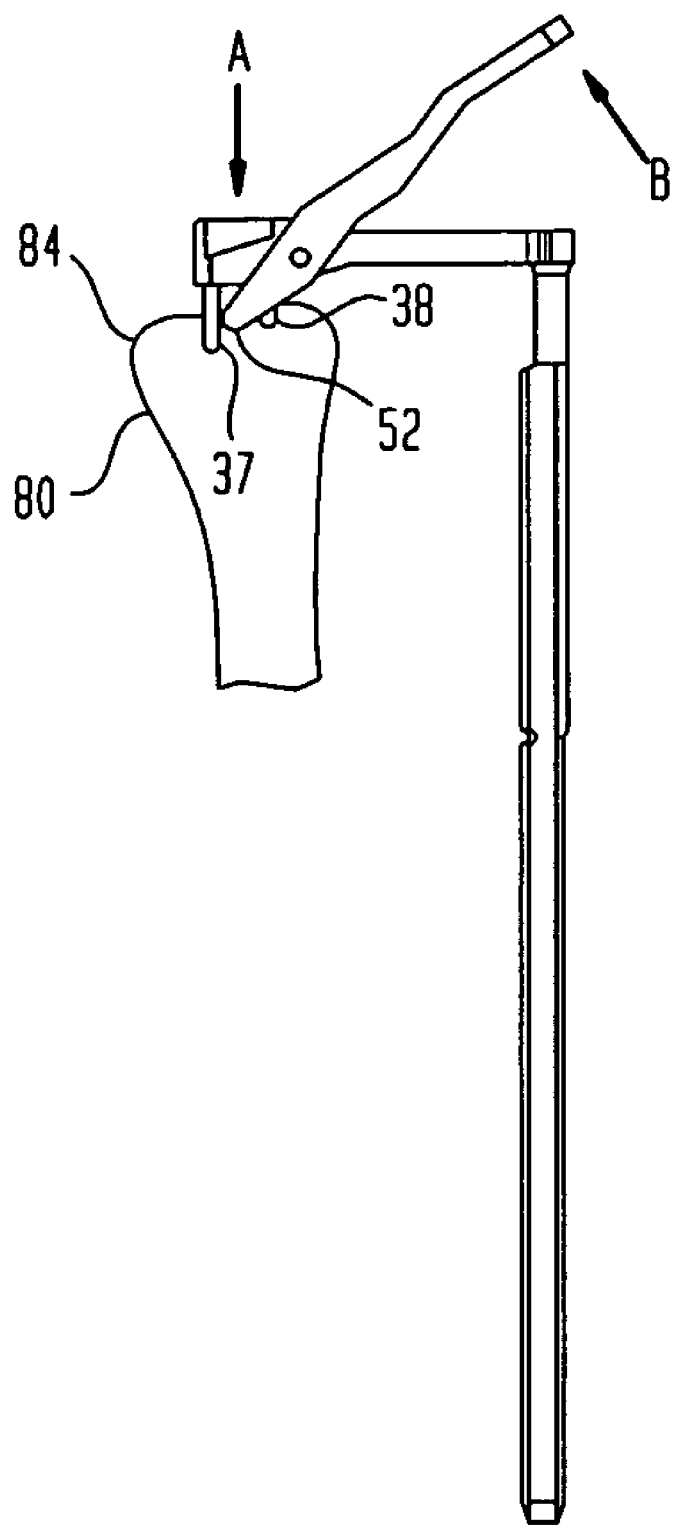
FIG. 6 is a perspective view illustrating the present invention in the engagement position.

The pivoting interaction between anchor arm 30 and extraction lever 50 enables the extraction lever to move from a release position, as shown in FIG. 5 to an actuation position, as shown in FIG. 6. In the actuation position, extraction lever 50 is placed in contact with a proximal end 84 of a tibia 80, as shown in FIG. 6.

Although not shown in the figures, tibial alignment guide assembly 10 also preferably includes an ankle clamp that is affixed to the distal end 16 of main shaft 12. The ankle clamp may be anyone of numerous ankle clamps known in the art. Additionally, although main shaft 12 of tibial alignment guide assembly 10 has been described with reference to a single embodiment, the present invention may be adapted to work with most main shaft embodiments known by those skilled in the art. For instance, the main shaft may include two telescopic rods that permit axial movement between one another. Further, the tibial alignment guide assembly may include a secondary shaft or secondary assembly that can provide an additional extramedullary reference plane for aiding in resecting the tibia. These alternative embodiments of the tibial alignment guide assembly are merely illustrative of the various tibial resection guide assemblies that may be employed in conjunction with the present invention and should not be considered as an exclusive list.

In a method of use, the tibial alignment guide assembly is positioned near the tibia of a leg with the resection guide placed in close proximity to the tibia and more specifically in close proximity to the medial tibia. The ankle clamp may next be affixed to the lower leg using techniques known in the art. Next, anchor pins 37, 38 are affixed to proximal end 84 of tibia 80. The tibial alignment guide assembly 10 is affixed to the tibia so that main shaft 12 parallels the long axis of the tibia in both the anterior/posterior view and the medial/lateral view.

In one such method of affixing tibial alignment guide assembly 10, anchor pins 37, 38 are driven into proximal end 84 of tibia 80 by exerting a force in the direction of arrow A against shield 39 of anchor arm 30, as shown in FIG. 5. Tibial alignment guide assembly 10 may now be used as an extramedullary reference and alignment guide for the positioning of resection guide 20.

With the help of main shaft 12 as a reference plane, resection guide 20 is adjusted relative to the tibia in order that the resection guide is able to direct a cutting instrument (not shown in the figures), such as an oscillating saw, along a correct cutting plane. The resection guide 20 is adjusted so as to direct the cutting instrument along the appropriate varus/valgus angle as well as the appropriate flexion/extension angle. Once resection guide 20 is in a desired position, the resection guide is affixed to tibia 80 by placing pins, screws or similar fixation means (not shown in the figures) through apertures 86 disposed along a wall 87 of the resection guide and into tibia 80. The pins anchor the resection guide 20 in a correct position relative to the tibia.

With resection guide 20 now correctly aligned, the rest of the tibial alignment guide assembly 10 may be removed so that the actual resecting of the tibia may be performed. Removing the rest of tibial alignment guide assembly 20 generally includes removing the ankle clamp (not shown in the figures) and disconnecting resecting guide 20 from main shaft 12. Additionally, anchor pins 37, 38 are extracted from proximal end 84 of tibia 80.

In order to extract anchor pins 37, 38, a force in the direction B is applied to handle 54 of extraction lever 50, as shown in FIG. 6. The resulting force pivots extraction lever 50 about pivot pin 70 bringing actuation end 52 and preferably both first extension 58 and second extension 60 into contact with proximal end 84 of tibia 80. By continuing to apply a force in the direction B, extraction lever 50 applies a resultant force against proximal end 84 of tibia 80, thereby causing anchor pins 37, 38 to be pried from the tibia.

By removing anchor pins 37, 38 in a controlled manner, resecting guide 20 (not shown in FIG. 6 for ease of illustration) remains secured and correctly positioned relative to the tibia. Additionally, since extraction lever 50 is positioned directly on tibial alignment guide assembly 10, various steps required in prior art methods of preparing a tibial plateau for a tibial implant are eliminated, thereby reducing the time and expense of the surgery.

Once all of the fixation devices of tibial alignment guide assembly 10 have been removed from the tibia, (except for the fixation pins of resecting guide 20) the various parts of the tibial alignment guide assembly are disassembled from the resecting guide and discarded. In one preferred embodiment, resecting guide 20 only allows for the initiation of the osteotomy with an oscillating saw. After initiating the osteotomy, resecting guide 20 is removed from the tibia and the tibia bone itself directs the oscillating saw along the correct resecting plane for the remainder of the proximal tibia resection.

Figure 9:
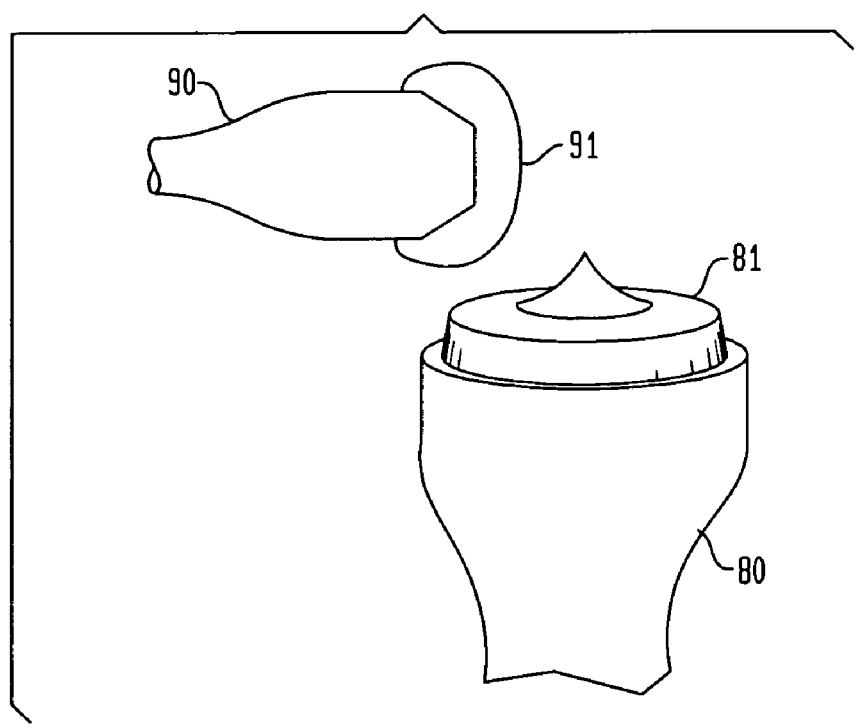
FIG. 9 illustrates a tibial implant and a femoral implant being positioned so as to reconstruct a knee joint.

As shown in FIG. 9, with the tibia plateau prepared to receive a tibial implant, the corresponding femoral bone may be resected. The femur may be resected using any method known by those skilled in the art such as that disclosed in U.S. Pat. No. 4,524,766, the disclosure of which is hereby incorporated by reference herein.

Subsequently, with both bones, i.e., the tibia 80 and femur 90 resected and prepared, a femoral implant 91 and tibial implant 81 may be attached to the femur and tibia respectively, in a manner known by those skilled in the art, so as to reconstruct a functioning knee joint. One such method is disclosed in U.S. Pat. No. 5,578,039, the disclosure of which is hereby incorporated by reference herein.

In another alternate embodiment, extraction lever 50 may only partially extract or pry anchor pins 37, 38 from tibia 80, thus necessitating an additional step to completely extract the anchor pins from the tibia. However, even if a hammer or other striking implement is required to force the anchor pins out from engagement with the tibia, since the anchor pins are at least partially removed by extraction lever 50, a much more controlled and stable force is only required by the hammer, thereby reducing the possibility of resection guide 20 becoming displaced from its desired position relative to the tibia.

With the resection guide correctly positioned and affixed to the tibia, and the rest of the tibial alignment guide assembly removed, the surgeon is now unencumbered and free to begin cutting the distal end of the tibia at the desired locations.

Figure 7A:
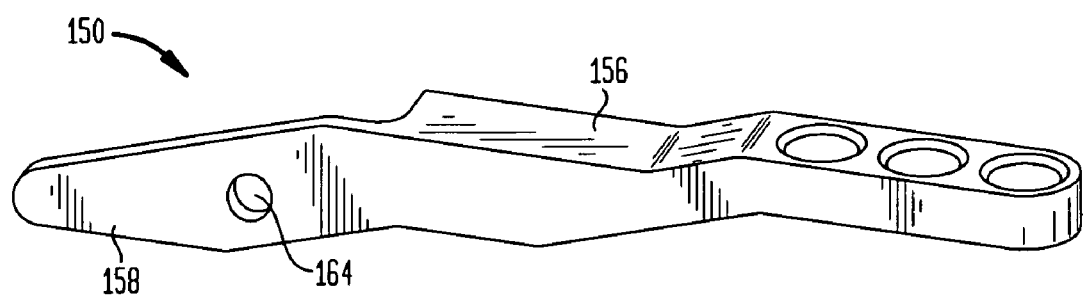
FIG. 7A illustrates an alternate embodiment of the extraction lever used in one embodiment of the present invention.

In an alternate embodiment of the tibial alignment guide assembly, the extraction lever may only include one extension. For example, as shown in FIG. 7A, extraction lever 150 may only include extension 158 extending outwardly from body 156. Extraction lever 150 may be similarly designed to extraction lever 50. For example, extension 158 includes an aperture 164 similar to first extension 58 of extraction lever 50. With only one extension and one aperture, as contrasted with the previous embodiment, a pivot pin for pivotally connecting anchor arm 130 to extraction lever 150 may be immovably mounted to anchor arm 130.

Figure 7B:
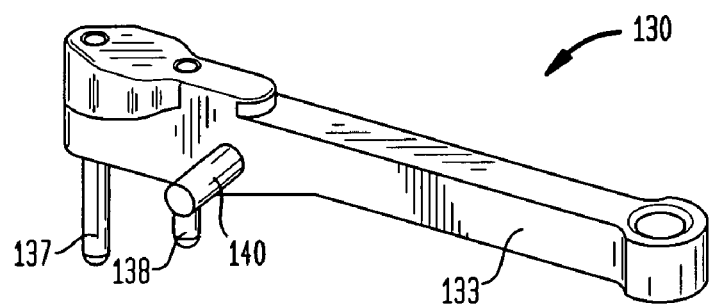
FIG. 7B illustrates an alternate embodiment of the anchor arm used in one embodiment of the present invention.

For example, as shown in FIG. 7B anchor arm 130 is provided with a pivot pin 140 extending radially outward from sidewall 133. Anchor arm 130 includes many of the same features of anchor arm 30, including anchor pins 137, 138.

In a method of assembly, aperture 164 of first extension 158 slidably receives pivot pin 140 therein. Extraction lever 150 may remain connected to anchor arm 130 in this removable manner or a nut or similar fastening means (not shown) may be provided to engage pivot pin 140 so that the extraction lever is more permanently connected to the anchor arm. With pivot pin 140 of anchor arm 130 received within aperture 164 of extraction lever 150, the extraction lever is pivotally attached to the anchor arm and capable of prying anchor pins 137, 138 from a tibia as illustrated in conjunction with previous embodiments.

Figure 8:
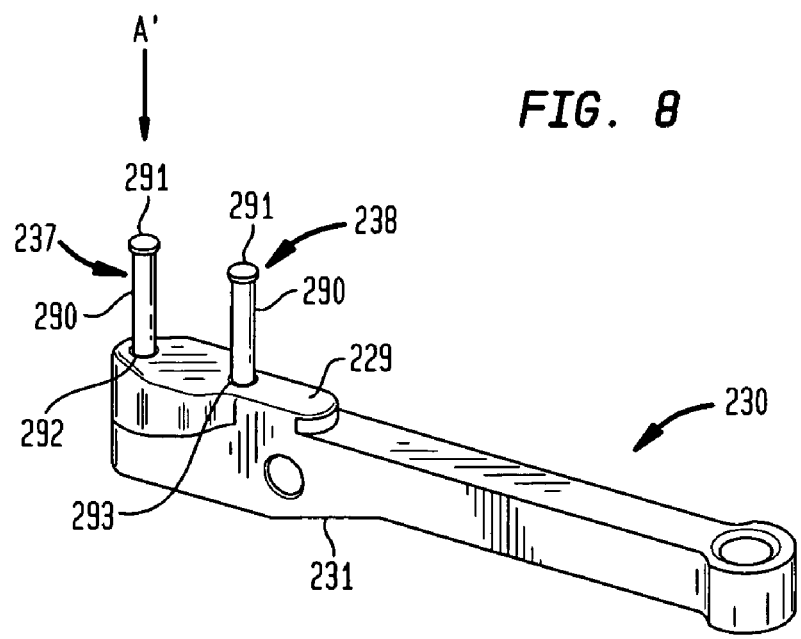
FIG. 8 illustrates an alternate embodiment of an anchor arm used in one embodiment of the present invention.

In still yet another alternate embodiment, the anchor pins may be discrete elements from the anchor arm. For example, as shown in FIG. 8, anchor pins 237, 238 may be provided with anchor arm 230. Anchor pins 237, 238 preferably include shafts 290 and caps 291. Anchor arm 230 includes two apertures 292, 293 extending from a top surface 229 to a bottom surface 231 of the anchor arm.

In a method of assembly, anchor pins 237, 238 are slidably received with respective apertures 292, 293. Much in the same way as illustrated with reference to previous embodiments, anchor pins 237, 238 may be affixed to the tibia by exerting a force in the direction of A' against the anchor pins, thereby causing the anchor pins to slide through the apertures of anchor arm 230 and into engagement with the tibia. Caps 291 of anchor pins 237, 238 limit the ability of the anchor pins to translate through the entire anchor arm.

Although not shown in the figures, when required the extraction lever may be used to urge the anchor pins from the tibia, as previously described. As the extraction lever exerts a force against the tibia, a resultant force causes the anchor arm to apply an upwards pressure against caps 291 of anchor pins 237, 238. This pressure subsequently begins to extract anchor pins 237, 238 from the tibia.

The present invention has been described with reference to extracting fixation devices from a tibial bone and more specifically form the tibial plateau. However, the present invention may be adapted to be mounted on various instruments and assemblies that require fixation devices to be removed from engagement with a bone in a controlled and steady manner.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A tibial alignment guide assembly for positioning a resection guide, the assembly comprising:

a main shaft having a proximal end and a distal end, said main shaft being adapted for juxtaposition with a tibia to assist in the positioning of the resection guide;

an anchor arm having an engaging end and a connection end, said connection end being attached to said proximal end of said main shaft, said engaging end having at least one anchor pin extending outwardly therefrom, said at least one anchor pin adapted to anchor the tibial alignment guide assembly to a tibia plateau in order that the resection guide may be correctly aligned to the tibia; and a lever including an actuation end and a handle, said lever being pivotally connected to said anchor arm, whereby movement of said lever while said actuation end bears against the tibial plateau surface causes at least the partial extraction of said at least one anchor pin from the tibial plateau.

2. The tibial alignment guide assembly according to claim 1, further comprising a pivot pin, wherein said anchor arm includes a first aperture extending therethrough, and said lever includes a second aperture extending therethrough, wherein said first aperture and said second aperture are concentric and receive said pivot pin therein, such that said anchor arm and said lever are pivotally connected.

3. The tibial alignment guide assembly according to claim 1, further comprising a pivot pin, wherein said anchor arm includes a first aperture, wherein said actuation end of said lever is bifurcated and includes a first extension having a second aperture and a second extension having a third aperture, said first extension and said second extension forming a gap therebetween, wherein said anchor arm is disposed within said gap so that said first aperture, said second aperture and said third aperture are concentric and receive said pivot pin therein.

4. The tibial alignment guide assembly according to claim 1, wherein said anchor arm includes an exterior surface and a pivot pin extending radially outward from said exterior surface, said lever including at least one aperture, wherein said pivot pin of said anchor arm is received within said aperture of said lever such that said anchor arm and said lever are pivotally connected.

5. The tibial alignment guide assembly according to claim 1, further comprising a resection guide connectable to said main shaft.

6. The tibial alignment guide assembly according to claim 1, wherein said at least one anchor pin is integral with said anchor arm.

7. A bone alignment guide assembly comprising:

a main shaft having a proximal end and a distal end, said main shaft being adapted for juxtaposition with a bone to assist in the positioning of a resection guide;

an anchor arm attached to said proximal end of said main shaft, said anchor arm including at least one engagement pin adapted for engaging a surface of a bone such that the bone alignment guide assembly is affixed to the bone; and a lever mounted on the anchor arm including extraction means having a bone contacting surface for contacting a bone surface adjacent the at least one engagement pin initiating extraction of said at least one engagement pin of said anchor arm from the bone.

8. The bone alignment guide assembly according to claim 7, wherein said lever is pivotally mounted on said anchor arm.

9. The bone alignment guide assembly according to claim 7, further comprising a resection guide connectable to the bone alignment guide.

10. The bone alignment guide assembly according to claim 7, wherein the bone is a tibia.

11. A method of preparing a patient's proximal tibia for surgery, the method comprising the steps of:
   positioning a resection guide in a desired spatial relationship relative to the tibia;
   anchoring a tibial alignment guide assembly to a proximal tibia with a pin engaging a proximally facing surface of the tibia;
   aligning the resection guide with the alignment guide and securing said resection guide to the tibia; and
   initiating removal of at least the pin of said tibial alignment guide assembly from the proximal tibia by actuating a lever mounted thereon and moving the lever into engagement with the surface of the tibia engaged by the pin.

12. The method according to claim 11, wherein the tibial alignment guide assembly includes an anchor arm having at least one anchor pin, wherein the step of anchoring said tibial alignment guide assembly includes urging said at least one anchor pin into engagement with the proximal tibia, and wherein said step of initiating removal of at least a portion of said tibial alignment guide assembly includes initiating removal of said at least one anchor pin from engagement with the proximal tibia.

13. The method according to claim 11, wherein said lever is pivotally connected to said anchor arm.

14. The method according to claim 11, wherein said actuating of said lever includes bringing said lever into contact with the proximal tibia.

15. The method according to claim 11, wherein said lever is pivotally connected to the tibial alignment guide assembly.

16. A method of reconstructing a knee joint comprising:
   positioning a resection guide in a desired spatial relationship relative to a tibia;
   anchoring a tibial alignment guide assembly to a proximal tibia with a pin engaging a proximally facing surface of the tibia;
   aligning the resection guide with the alignment guide and securing said resection guide to the tibia;
   initiating removal of at least a portion of said tibial alignment guide assembly from the proximal tibia by actuating a lever connected to said tibial alignment guide assembly and engaging a bone contacting surface on the lever with the surface of the tibia engaged by the pin;
   continuing to prepare the proximal tibia to receive a tibial implant;
   preparing a femur to receive a femoral implant; and
   implanting said tibial implant and said femoral implant so as to reconstruct a knee joint.

17. The method according to claim 16, further comprising preparing a patella to receive a patella implant and implanting said patella implant.

* * * * *